United States Patent
Shimizu et al.

(10) Patent No.: US 7,368,413 B2
(45) Date of Patent: May 6, 2008

(54) HERBICIDAL COMPOSITION AND METHOD OF USING THE SAME

(75) Inventors: Toshiaki Shimizu, Kawachinagano (JP); Miyako Aoki, Osaka (JP); Isao Ishimura, Yao (JP); Tsutomu Mabuchi, Osakasayama (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 360 days.

(21) Appl. No.: 10/498,093

(22) PCT Filed: Dec. 19, 2002

(86) PCT No.: PCT/JP02/13291

§ 371 (c)(1), (2), (4) Date: Jun. 10, 2004

(87) PCT Pub. No.: WO03/051117

PCT Pub. Date: Jun. 26, 2003

(65) Prior Publication Data

US 2005/0085387 A1    Apr. 21, 2005

(30) Foreign Application Priority Data

Dec. 19, 2001 (JP) ............................. 2001-386057

(51) Int. Cl.
*A01N 25/00* (2006.01)
*A01N 43/00* (2006.01)
*A01N 43/36* (2006.01)
*A01N 57/18* (2006.01)
*A01N 43/56* (2006.01)

(52) U.S. Cl. .................. 504/116.1; 504/129; 504/138; 504/139; 504/286; 504/206; 504/282

(58) Field of Classification Search ............... 504/128, 504/139, 206, 282, 116.1, 129, 138, 286
See application file for complete search history.

(56) References Cited

U.S. PATENT DOCUMENTS

| 5,888,934 A | * | 3/1999 | Townson et al. ............ 504/206 |
| 6,720,288 B1 | * | 4/2004 | Kanayama et al. ......... 504/128 |
| 6,774,087 B1 | * | 8/2004 | Nakayama et al. ......... 504/273 |

FOREIGN PATENT DOCUMENTS

| JP | 07-242510 | * | 9/1995 |
| WO | WO 00/64258 | * | 11/2000 |

OTHER PUBLICATIONS

Robyn E. Gaskin, et al.; "Some Physicochemical Factors Influencing Follar Uptake Enhancement of Glyphosate-Mono(Isopropylammonium) by Polyoxyethylene Surfactants"; 1992; vol. 34, No. 3, pp. 195-206.

* cited by examiner

*Primary Examiner*—Sreeni Padmanabhan
*Assistant Examiner*—Umamaheswar Ramachandran
(74) *Attorney, Agent, or Firm*—Oliff & Berridge, PLC

(57) ABSTRACT

Herbicidal compositions containing as active ingredients, one or more compounds selected from light-induced herbicidal compounds, especially 3-substituted phenylpyrazole derivatives and one or more compounds selected from organophosphorus herbicidal compounds, characterized by containing as surfactants, one or more of alkenyl alcohol alkoxylates and one or more of alkyl alcohol alkoxylates; and methods of using the herbicidal compositions.

4 Claims, No Drawings

HERBICIDAL COMPOSITION AND METHOD OF USING THE SAME

TECHNICAL FIELD

The present invention relates to a herbicidal composition having a rapid action, an improved effect and a long-term stability of preparation, and a method of using the herbicidal composition.

BACKGROUND ART

Among the light-induced herbicidal compounds represented by the general formula (I), 3-substituted phenylpyrazole derivatives represented by the general formula (I-1) are known compounds disclosed in Japanese Patent Laid-open Nos. Hei 3-163063 and Hei 4-211085, wherein it is mentioned that these compounds have, as herbicides for foliage treatment, an outstanding herbicidal activity on general broad-leaved weeds noxious in upland farming.

It is known that a number of compounds analogous to the chemical structure of the general formula (I-1) in the overall chemical structure and relative configuration of substituents exhibit a similar herbicidal activity as light-induced herbicides (Anderson et al., ACS Symposium Series, Vol. 559, Porphyric Pesticides, S. O. Duke and C. A. Robeiz eds., p. 18-34 (1994)). It is also known that a resistance to these light-induced herbicides can generally be given to plants by introducing a specific gene into the plants (International Patent Application WO98/29554).

On the other hand, organophosphorus herbicidal compounds such as N-(phosphonomethyl) glycine or salts thereof disclosed in Japanese Patent Laid-open Nos. Sho 47-39538 and Sho 57-98994, 4-[hydroxy(methyl)phosphino]-DL-homoalanine or salts thereof disclosed in Japanese Patent Laid-open No. Sho 57-26564 and 4-[hydroxy(methyl)phosphino]-L-homoalanyl-L-alanyl-L-alanine or salts thereof disclosed in Japanese Patent Laid-open No. Sho 50-23282, etc. are well known as non-selective herbicides for foliage treatment.

Further, Japanese Patent Laid-open No. Hei 7-242510 discloses herbicidal compositions containing a 3-substituted phenylpyrazole derivative and an organophosphorus herbicidal compound.

Further, Weed Sci. Soc. 25, (1977), p. 275-287 refers to an adjuvant effect of alkyl alcohol alkoxylates on N-(phosphonomethyl) glycine. However, this technique is insufficient in the adjuvant effect and the alkyl alcohol alkoxylates are not readily compatible with an aqueous solution of N-(phosphonomethyl) glycine.

Thus, it has been demanded to further improve the herbicidal effect and rapid action of a herbicidal composition containing a light-induced herbicidal compound, especially a 3-substituted phenylpyrazole derivative and an organophosphorus herbicidal compound.

DISCLOSURE OF INVENTION

The present inventors have conducted extensive studies with the aim of solving the problems mentioned above to find that, by adding an alkenyl alcohol alkoxylate and an alkyl alcohol alkoxylate as surfactants to a herbicidal composition containing one or more compounds selected from light-induced herbicidal compounds, especially one or more compounds selected from the 3-substituted phenylpyrazole derivatives represented by the general formula (I-1), and one or more compounds selected from organophosphorus herbicidal compounds as active ingredients, the rapid action of the composition can be made excellent and the effect of the composition can be improved by a synergistic action of the active ingredients and the surfactants, besides there can be obtained a herbicidal composition keeping stable herbicidal activity for a long period of time. Based on this finding, the present invention has been accomplished.

The present invention relates to a herbicidal composition containing one or more compounds selected from light-induced herbicidal compounds and one more compounds selected from organophosphorus herbicidal compounds as active ingredients, and containing an alkenyl alcohol alkoxylate and an alkyl alcohol alkoxylate as surfactants, and a method of using the herbicidal composition. Particularly, the present invention relates to a herbicidal composition containing, as active ingredients, the light-induced herbicidal compounds which are one or more compounds selected from the group consisting of the compounds represented by the general formula (I):

$$P-Q \qquad (I)$$

wherein P represents a group selected from $P^1$ to $P^{10}$:

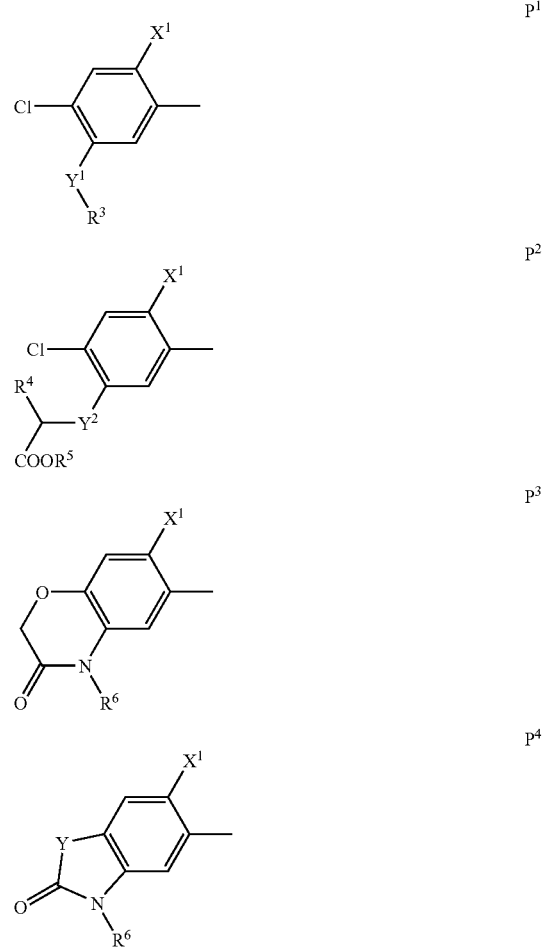

-continued

P⁵
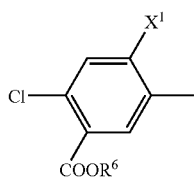

P⁶
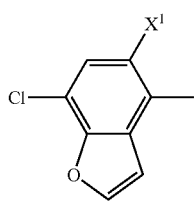

P⁷
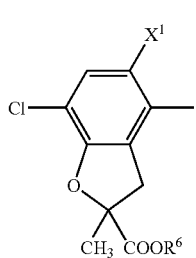

P⁸
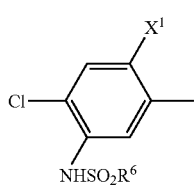

P⁹
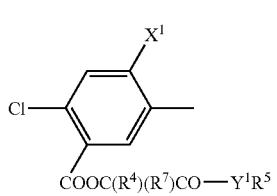

P¹⁰
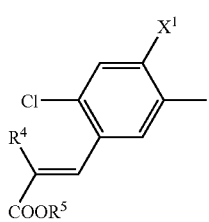

wherein $R^3$ represents a ($C_1$-$C_6$) alkyl group, a halo ($C_1$-$C_6$) alkyl group, a ($C_2$-$C_6$) alkenyl group or a ($C_2$-$C_6$) alkynyl group, $R^4$ represents a hydrogen atom, a halogen atom or a ($C_1$-$C_6$) alkyl group, $R^5$ represents a hydrogen atom, a ($C_1$-$C_6$) alkyl group, a halo ($C_1$-$C_6$) alkyl group, a ($C_2$-$C_6$) alkenyl group or a ($C_2$-$C_6$) alkynyl group, $R^6$ represents a ($C_1$-$C_6$) alkyl group, a ($C_2$-$C_6$) alkenyl group or a ($C_2$-$C_6$) alkynyl group, $R^7$ represents a hydrogen atom, a halogen atom or a ($C_1$-$C_6$) alkyl group, $X^1$ represents a hydrogen atom or a halogen atom, Y represents —O—, —S—, —SO— or —SO$_2$—, $Y^1$ represents —O—, —NH— or —S—, and $Y^2$ represents —O—, —S—, —NH— or —CH$_2$—;

Q represents $Q^1$ to $Q^{12}$:

Q¹
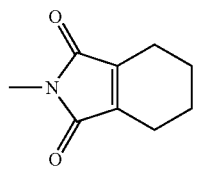

Q²
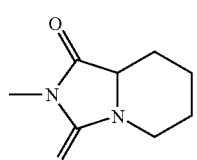

Q³
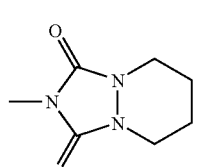

Q⁴
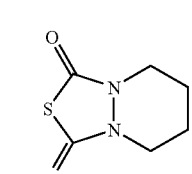

Q⁵
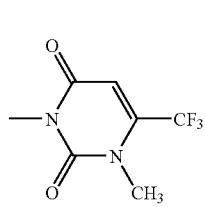

Q⁶
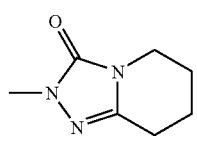

Q⁷
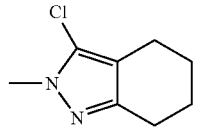

Q⁸
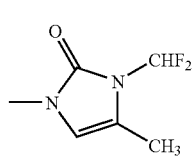

Q⁹
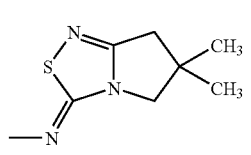

-continued

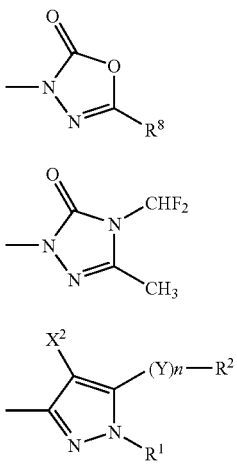

wherein R¹ represents a ($C_1$-$C_6$) alkyl group, R² represents a hydrogen atom, a ($C_1$-$C_6$) alkyl group or a halo ($C_1$-$C_6$) alkyl group, R⁸ represents a hydrogen atom or a ($C_1$-$C_6$) alkyl group, X² represents a halogen atom, Y is as defined above, and n represents an integer of 0 or 1;

and more particularly, one or more compounds selected from the group consisting of 3-substituted phenylpyrazole derivatives represented by the general formula (I-1)

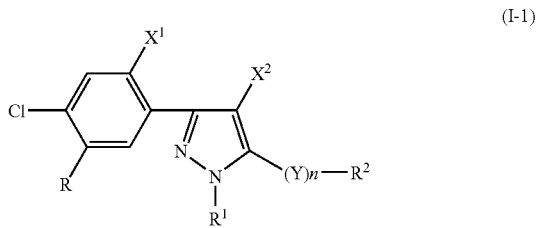

wherein R represents —Y¹—R³ (wherein R³ represents a ($C_1$-$C_6$) alkyl group, a halo ($C_1$-$C_6$) alkyl group, a ($C_2$-$C_6$) alkenyl group or a ($C_2$-$C_6$) alkynyl group and Y¹ represents —O—, —NH— or —S—), —Y²CH(R⁴)CO—OR⁵ (wherein R⁴ represents a hydrogen atom, a halogen atom or a ($C_1$-$C_6$) alkyl group, R⁵ represents a hydrogen atom, a ($C_1$-$C_6$) alkyl group, a halo ($C_1$-$C_6$) alkyl group, a ($C_2$-$C_6$) alkenyl group or a ($C_2$-$C_6$) alkynyl group, and y² represents —O—, —S—, —NH— or —CH₂—), —COOCH(R⁴)CO—Y¹R⁵ (wherein R⁴ represents a hydrogen atom, a halogen atom or a ($C_1$-$C_6$) alkyl group, R⁵ represents a hydrogen atom, a ($C_1$-$C_6$) alkyl group, a halo ($C_1$-$C_6$) alkyl group, a ($C_2$-$C_6$) alkenyl group or a ($C_2$-$C_6$) alkynyl group, Y¹ represents —O—, —NH— or —S—), or —COOR⁶ (wherein R⁶ represents a ($C_1$-$C_6$) alkyl group, a ($C_2$-$C_6$) alkenyl group or a ($C_2$-$C_6$) alkynyl group), R¹ represents a ($C_1$-$C_6$) alkyl group, R² represents a hydrogen atom, a ($C_1$-$C_6$) alkyl group or a halo ($C_1$-$C_6$) alkyl group, X¹ represents a hydrogen atom or a halogen atom, X² represents a halogen atom, Y represents —O—, —S—, —SO— or —SO₂—, and n represents an integer of 0 to 1; and one or more compounds selected from the group consisting of organophosphorus herbicidal compounds, and further containing, as surfactants, an alkenyl alcohol alkoxylate and an alkyl alcohol alkoxylate; and further the present invention relates to a method of using the herbicidal composition.

Among the substituents in the general formula (I) and general formula (I-1), the ($C_1$-$C_6$) alkyl group means a straight or branched chain alkyl group having 1-6 carbon atoms such as methyl, ethyl, n-propyl, i-propyl, n-butyl, i-butyl, s-butyl, t-butyl, n-pentyl, n-hexyl and the like; the halo ($C_1$-$C_6$) alkyl group means a straight or branched chain alkyl group having 1-6 carbon atoms substituted with one or more halogen atoms which are selected from the group consisting of chlorine atom, fluorine atom, iodine atom and bromine atom and may be the same or different; the ($C_2$-$C_6$) alkenyl group means a straight or branched chain alkenyl group having 2-6 carbon atoms; and the ($C_2$-$C_6$) alkynyl group means a straight or branched chain alkynyl group having 2-6 carbon atoms.

The light-induced herbicidal compounds in the present invention include for example the followings:

(1) N-[4-chloro-2-fluoro-5-(1-methyl-prop-2-ynyloxy)phenyl]-3,4,5,6-tetrahydrophthalimide (common name: flumipropyn)

(2) pentyl[2-chloro-5-(cyclohexa-1-ene-1,2-dicarboximide)-4-fluorophenoxy]-acetate (common name: flumiclorac-pentyl)

(3) N-(7-fluoro-3,4-dihydro-3-oxo-4-prop-2-ynyl-2H-1,4-benzoxazin-6-yl)cyclohex-1-ene-1,2-dicarboxamide (common name: flumioxazin)

(4) ethyl(RS)-2-chloro-3-[2-chloro-5-(4-difluoromethyl-4,5-dihydro-3-methyl-5-oxo-1H-1,2,4-triazol-1-yl)-4-fluorophenyl]propionate (common name: carfentrazone-ethyl)

(5) 2',4'-dichloro-5'-(4-difluoromethyl-4,5-dihydro-3-methyl-5-oxo-1H-1,2,4-triazol-1-yl)methanesulfonanilide (common name: sulfentrazone)

(6) 2-(2,4-dichloro-5-prop-2-yloxyphenyl)-5,6,7,8-tetrahydro-1,2,4-triazolo[4,3-a]pyridin-3(2H)-one (common name: azafenidin)

(7) methyl[2-chloro-4-fluoro-5-(tetrahydro-3-oxo-1H,3H-[1,3,4]thiadiazolo[3,4-a]pyridazin-1-ylideneamino)phenylthio]acetate (common name: fluthiacet-methyl)

(8) 6[(3Z)-6,7-dihydro-4,4-dimethyl-3H,5H-pyrrolido[2,1-c][1,2,4]thiadiazol-7-ylideneamino]-7-fluoro-4-(2-propynyl)-2H-1,4-benzoxadin-3(4H)-one (common name: thidiazimin)

(9) 5-tert-butyl-3-(2,4-dichloro-5-isopropoxyphenyl)-1,3,4-oxadiazol-2(3H)-one (common name: oxadiazon)

(10) 5-tert-butyl-3-[2,4-dichloro-5-(prop-2-ynyloxy)phenyl]-1,3,4-oxadiazol-(3H)-one (common name: oxadiargyl)

(11) ethyl(Z)-2-chloro-3-[2-chloro-5-(cyclohex-1-ene-1,2-dicarboximido)phenyl]acrylate (common name: cinidon-ethyl)

(12) 1-(allyloxycarbonyl)-1-methylethyl 2-chloro-5-[1,2,3,6-tetrahydro-3-methyl-2,6-dioxo-4-(trifluoromethyl)pyrimidin-1-yl]benzoate (common name: butafenacil), and further the following 3-substituted phenylpyrazole derivatives represented by the general formula (I-1).

TABLE 1

General Formula (I-1) (I-1)

[Structure: 4-Cl, 5-R substituted phenyl attached to pyrazole ring with X¹ at ortho position; pyrazole has X² at 4-position, (Y)n—R² at 5-position, and R¹ on N]

($R^1$ = $CH_3$)

| No. | R | $R^2$ | $X^1$ | $X^2$ | (Y)n | Physical Property |
|---|---|---|---|---|---|---|
| 1 | $OCH_2CH=CH_2$ | $CH_3$ | Cl | Cl | S | nD 1.6131(25.3° C.) |
| 2 | $OCH_2CH=CH_2$ | $CHF_2$ | Cl | Cl | O | nD 1.5536(28.4° C.) |
| 3 | $OCH_2CH=CH_2$ | $CHF_2$ | F | Cl | O | m.p. 63.7-64.1° C. |
| 4 | $SCH_2CH=CH_2$ | $CH_3$ | Cl | Cl | S | Paste |
| 5 | $SCH_2CH=CH_2$ | $CHF_2$ | Cl | Cl | O | m.p. 52.0-55.0° C. |
| 6 | $SCH_2CH=CH_2$ | $CHF_2$ | F | Cl | O | nD 1.5670(17.9° C.) |
| 7 | $OCH_2C\equiv CH$ | $CH_3$ | Cl | Cl | S | m.p. 71.5° C. |
| 8 | $OCH_2C\equiv CH$ | $CHF_2$ | Cl | Cl | O | m.p. 84.0° C. |
| 9 | $OCH_2C\equiv CH$ | $CHF_2$ | F | Cl | O | m.p. 98.0-98.1° C. |
| 10 | $SCH_2C\equiv CH$ | $CH_3$ | Cl | Cl | S | m.p. 94.5° C. |
| 11 | $SCH_2C\equiv CH$ | $CHF_2$ | Cl | Cl | O | m.p. 127-129° C. |
| 12 | $SCH_2C\equiv CH$ | $CHF_2$ | F | Cl | O | m.p. 82.8° C. |
| 13 | $OCH_2COOCH_3$ | $CH_3$ | Cl | Cl | S | m.p. 126.2° C. |
| 14 | $OCH_2COOCH_3$ | $CHF_2$ | Cl | Cl | O | m.p. 119.8° C. |
| 15 | $OCH_2COOCH_3$ | $CHF_2$ | Cl | Br | O | m.p. 133.8° C. |
| 16 | $OCH_2COOCH_3$ | $CHF_2$ | F | Cl | O | m.p. 122.8-123.1° C. |
| 17 | $OCH_2COOCH_2CH_3$ | $CH_3$ | Cl | Cl | S | m.p. 106.5° C. |
| 18 | $OCH_2COOCH_2CH_3$ | $CHF_2$ | Cl | Cl | O | m.p. 102.3° C. |
| 19 | $OCH_2COOCH_2CH_3$ | $CHF_2$ | F | Cl | O | m.p. 127.6° C. |
| 20 | $OCH_2COOC_3H_7$-n | $CHF_2$ | Cl | Cl | O | m.p. 89.7° C. |
| 21 | $OCH_2COOC_3H_7$-n | $CHF_2$ | F | Cl | O | m.p. 97.6-97.8° C. |
| 22 | $OCH_2COOC_3H_7$-i | $CHF_2$ | Cl | Cl | O | m.p. 106.0° C. |
| 23 | $OCH_2COOC_3H_7$-i | $CHF_2$ | F | Cl | O | m.p. 120.3-120.5° C. |
| 24 | $OCH_2COOCH_2CH=CH_2$ | $CHF_2$ | Cl | Cl | O | m.p. 84.7° C. |
| 25 | $OCH_2COOCH_2CH=CH_2$ | $CHF_2$ | F | Cl | O | m.p. 89.2-89.4° C. |
| 26 | $OCH_2COOCH_2C\equiv CH$ | $CHF_2$ | Cl | Cl | O | m.p. 119.6° C. |
| 27 | $OCH_2COOCH_2C\equiv CH$ | $CHF_2$ | F | Cl | O | m.p. 99.0° C. |
| 28 | $OCH(CH_3)COOH$ | $CH_3$ | Cl | Cl | S | m.p. 191-194° C. |
| 29 | $OCH(CH_3)COOCH_3$ | $CH_3$ | Cl | Cl | S | m.p. 90-93° C. |
| 30 | $OCH(CH_3)COOCH_3$ | $CHF_2$ | F | Cl | O | m.p. 95.6° C. |
| 31 | $OCH(CH_3)COOC_2H_5$ | $CH_3$ | Cl | Cl | S | nD 1.5763(28.8° C.) |
| 32 | $OCH(CH_3)COOC_2H_5$ | $CHF_2$ | Cl | Cl | O | nD 1.5238(25.7° C.) |
| 33 | $OCH(CH_3)COOC_2H_5$ | $CHF_2$ | Cl | Br | O | nD 1.5396(20.8° C.) |
| 34 | $OCH(CH_3)COOC_2H_5$ | $CHF_2$ | F | Cl | O | m.p. 67.0-67.2° C. |
| 35 | $OCH(CH_3)COOC_3H_7$-i | $CH_3$ | Cl | Cl | S | m.p. 87-90° C. |
| 36 | $SCH(CH_3)COOCH_3$ | $CHF_2$ | Cl | Cl | O | nD 1.5654(19.8° C.) |
| 37 | $SCH(CH_3)COOCH_3$ | $CHF_2$ | F | Cl | O | nD 1.5494(25.0° C.) |
| 38 | $SCH(CH_3)COOC_2H_5$ | $CHF_2$ | Cl | Cl | O | nD 1.5565(28.0° C.) |
| 39 | $SCH(CH_3)COOC_2H_5$ | $CHF_2$ | F | Cl | O | nD 1.5328(18.0° C.) |
| 40 | $NHCH(CH_3)COOCH_3$ | $CH_3$ | Cl | Cl | S | m.p. 144.2° C. |
| 41 | $NHCH(CH_3)COOC_2H_5$ | $CH_3$ | Cl | Cl | S | Paste |
| 42 | $NHCH(CH_3)COOC_2H_5$ | $CHF_2$ | Cl | Cl | O | nD 1.5371(23.4° C.) |
| 43 | $NHCH(CH_3)COOC_2H_5$ | $CHF_2$ | F | Cl | O | nD 1.5264(26.6° C.) |
| 44 | $COOCH_2COOCH_3$ | $CHF_2$ | Cl | Cl | O | m.p. 74.4° C. |
| 45 | $COOCH_2COOCH_3$ | $CHF_2$ | F | Cl | O | nD 1.5350(27.3° C.) |
| 46 | $COOCH_2COSCH_3$ | $CHF_2$ | Cl | Cl | O | |
| 47 | $COOCH_2COSCH_3$ | $CHF_2$ | F | Cl | O | |
| 48 | $COOCH_2COOC_2H_5$ | $CHF_2$ | Cl | Cl | O | m.p. 57.2° C. |
| 49 | $COOCH_2COOC_2H_5$ | $CHF_2$ | F | Cl | O | nD 1.5362(23.4° C.) |
| 50 | $COOCH_2COSC_2H_5$ | $CHF_2$ | Cl | Cl | O | nD 1.5763(20.7° C.) |
| 51 | $COOCH_2COSC_2H_5$ | $CHF_2$ | F | Cl | O | nD 1.5536(27.3° C.) |
| 52 | $COOCH_2COOC_3H_7$-i | $CHF_2$ | Cl | Cl | O | nD 1.5289(24.0° C.) |
| 53 | $COOCH_2COOC_3H_7$-i | $CHF_2$ | F | Cl | O | |
| 54 | $COOCH_2COSC_3H_7$-i | $CHF_2$ | Cl | Cl | O | nD 1.5684(20.2° C.) |
| 55 | $COOCH_2COSC_3H_7$-i | $CHF_2$ | F | Cl | O | |
| 56 | $COOCH_2COOCH_2CH=CH_2$ | $CHF_2$ | Cl | Cl | O | m.p. 45.4° C. |
| 57 | $COOCH_2COOCH_2CH=CH_2$ | $CHF_2$ | F | Cl | O | |
| 58 | $COOCH_2COOCH_2C\equiv CH$ | $CHF_2$ | Cl | Cl | O | m.p. 79.3° C. |
| 59 | $COOCH_2COOCH_2C\equiv CH$ | $CHF_2$ | F | Cl | O | |
| 60 | $COOCH(CH_3)COOCH_3$ | $CHF_2$ | Cl | Cl | O | nD 1.5370(25.7° C.) |
| 61 | $COOCH(CH_3)COOCH_3$ | $CHF_2$ | F | Cl | O | nD 1.5314(23.0° C.) |

TABLE 1-continued

General Formula (I-1)

($R^1$ = $CH_3$)

| No. | R | $R^2$ | $X^1$ | $X^2$ | (Y)n | Physical Property |
|---|---|---|---|---|---|---|
| 62 | COOCH($CH_3$)COO$C_2H_5$ | $CHF_2$ | Cl | Cl | O | nD 1.5672(26.0° C.) |
| 63 | COOCH($CH_3$)COO$C_2H_5$ | $CHF_2$ | F | Cl | O | nD 1.5212(14.1° C.) |
| 64 | COOCH$_2$C≡CH | $CHF_2$ | Cl | Cl | O | m.p. 78.5° C. |
| 65 | COOCH$_3$ | $CHF_2$ | Cl | Cl | O | m.p. 63.9° C. |
| 66 | COOCH$_3$ | $CHF_2$ | F | Cl | O | nD 1.5430(17.0° C.) |
| 67 | COO$C_2H_5$ | $CH_3$ | Cl | Cl | S | nD 1.6029(20.1° C.) |
| 68 | COO$C_2H_5$ | $CHF_2$ | Cl | Cl | O | nD 1.5446(26.8° C.) |
| 69 | COO$C_2H_5$ | $CHF_2$ | F | Cl | O | nD 1.5320(21.0° C.) |
| 70 | OCH$_2$CH=CH$_2$ | $CHF_2$ | Cl | Cl | NH | m.p. 80.6° C. |
| 71 | OCH$_2$C≡CH | $CHF_2$ | Cl | Cl | NH | m.p. 118.9° C. |
| 72 | OCH$_2$COOCH$_3$ | i-$C_7H_7$ | Cl | Cl | — | Paste |
| 73 | OCH$_2$CH=CH$_2$ | i-$C_3H_7$ | Cl | Cl | — | Paste |
| 74 | OCH$_2$C≡CH | i-$C_3H_7$ | Cl | Cl | — | Paste |
| 75 | SCH$_2$COOCH$_3$ | t-$C_4H_9$ | Cl | Cl | — | Paste |
| 76 | OCH$_2$CH=CH$_2$ | CH$_2$Br | Cl | Cl | — | Paste |

Among the 3-substituted phenylpyrazole derivatives in the present invention represented by the general formula (I-1), the compound No. 19 is preferred.

On the other hand, the organophosphorus herbicidal compounds used in the present invention include, for example N-(phosphonomethyl) glycine or salts thereof, such as N-(phosphonomethyl) glycine isopropylamine salt (hereinafter, referred to as "compound A"), N-(phosphonomethyl) glycine ammonium salt, N-(phosphonomethyl) glycine trimethyl sulfonium salt, N-(phosphonomethyl) glycine potassium salt; 4-[hydroxy(methyl)phosphino]-DL-homoalanine or salts thereof, such as 4-[hydroxy(methyl)phosphino]-DL-homoalanine ammonium salt; 4-[hydroxy(methyl)phosphino]-L-homoalanyl-L-alanyl-L-alanine or salts thereof, such as 4-[hydroxy(methyl)phosphino]-L-homoalanyl-L-alanyl-L-alanine sodium salt, etc. Preferred organophosphorus herbicidal compounds are N-(phosphonomethyl) glycine isopropylamine salts.

The alkenyl alcohol alkoxylates used as a surfactant in the present invention include compounds represented by the general formula (II):

$$C_aH_{2a-1}\text{-}(Eo)_b(Po)_d\text{—OH} \quad (II)$$

wherein Eo represents —O—CH$_2$CH$_2$—, Po represents —O—CH(CH$_3$)CH$_2$—, and a, b and d represent integers of 1 to 20 which are the same or different from each other. The concrete examples thereof are an adduct of oleyl alcohol with polyoxyethylene, an adduct of oleyl alcohol with polyoxypropylene or a copolymer of oleyl alcohol, polyoxyethylene and polyoxypropylene. Preferable examples thereof include Noigen ET-89 (manufactured by Dai-ichi Kogyo Seiyaku Co., Ltd.), Noigen ET-109 (manufactured by the same company as above), Noigen ET-129 (manufactured by the same company as above), Noigen ET-149 (manufactured by the same company as above), Noigen ET-159 (manufactured by the same company as above), Pegnol O-107 (manufactured by Toho Chemical Industry Co., Ltd.) and Emulgen 409P (manufactured by Kao Corporation). One or more species of the above-mentioned alkenyl alcohol alkoxylates may be selected and put to use.

In addition, the alkyl alcohol alkoxylates include compounds represented by the general formula (III):

$$C_eH_{2e+1}\text{-}(Eo)_f(Po)_g\text{—OH} \quad (III)$$

wherein Eo represents —O—CH$_2$CH$_2$—, Po represents —O—CH(CH$_3$)CH$_2$—, and e, f and g represent integers of 1 to 20 which are the same or different from each other. Concrete examples thereof include primary alkyl alcohol ethoxylates, primary alkyl alcohol propoxylates, primary alkyl alcohol ethoxylate propoxylates, secondary alkyl alcohol ethoxylates, secondary alkyl alcohol propoxylates, secondary alkyl alcohol ethoxylate propoxylates, tertiary alkyl alcohol ethoxylates, tertiary alkyl alcohol propoxylates or tertiary alkyl alcohol ethoxylate propoxylates. Preferable examples thereof include Noigen ET-165 (manufactured by Dai-ichi Kogyo Seiyaku Co., Ltd.), Noigen ET-105 (manufactured by the same company as above), Adekatol SO-135 (manufactured by Asahi Denka Co., Ltd.), NK (Newkalgen)-D-1107S (manufactured by Takemoto Oil & Fat Co., Ltd), Lutensol T08 (manufactured by BASF AG), TO-347 (manufactured by Nippon Nyukazai Co., Ltd.), etc. One or more species of such alkyl alcohol alkoxylates may be selected and put to use.

In the herbicidal composition of the present invention, compounding ratios of the ingredients are as follows. That is, in 100 parts by weight of the herbicidal composition, the light-induced herbicidal compound is used in an amount of 0.01-10.0 parts by weight and preferably 0.1-2.0 parts by weight; the organophosphorus herbicidal compound is used in an amount of 1.0-60.0 parts by weight and preferably 5.0-40.0 parts by weight; the alkenyl alcohol alkoxylate is used in an amount of 0.1-20 parts by weight and preferably 5.0-15.0 parts by weight; and the alkyl alcohol alkoxylate is used in an amount of 0.1-20.0 parts by weight and preferably 5.0-15.0 parts by weight.

The compounding ratios of the alkenyl alcohol alkoxylate and alkyl alcohol alkoxylate in the herbicidal composition of the present invention are 5/1 to 1/5, preferably 2/1 to 1/2 in the weight of the alkenyl alcohol alkoxylate/the weight of alkyl alcohol alkoxylate.

When the herbicidal composition of the present invention is put to use, the composition is made into an appropriate preparation form in accordance with the purpose according to the conventional method in the pesticide preparation, and then put to use. For instance, the composition is blended with a solid carrier, a liquid carrier or other necessary adjuvants, and the blended mixture thus obtained is made into a preparation form such as a suspension concentrate in which the active ingredients exist in a state of suspended fine particles, or a wettable powder, or a water dispersible granule, or the like and then put to use.

Further, it is also possible to blend a preparation composition containing surfactants to be used in the present invention in an amount of 0.1-99.0 parts by weight, preferably 25.0-75.0 parts by weight per part by weight of the light-induced herbicide compound of general formula (I), with a commercially available preparation containing an organophosphorus compound as an active ingredient, at the time of preparing a liquid preparation to be sprayed, and thereafter to put to use.

When using a suspension concentrate or a water dispersible granule which contains a finely pulverized material comprising as active ingredients 0.01-10 parts by weight of the light-induced herbicidal compound represented by the general formula (I) and 1-50 parts by weight of an organophosphorus herbicidal compound and which contains no surfactant, it is also possible to mix and dissolve separately surfactants to be used in the present invention in the suspension concentrate or water dispersible granule at the time of preparing a liquid mixture to be sprayed, at a ratio of 10-90 parts by weight of the surfactant solution per part by weight of the light-induced herbicidal compound represented by the general formula (I).

BEST MODE FOR CARRYING OUT THE INVENTION

Typical examples and test examples of the present invention will be presented below. The present invention is by no means limited by these examples. In the meanwhile, the term "part" and "parts" mean part by weight or parts by weight, respectively.

(Base)

| | |
|---|---|
| Compound No. 19 | 40.0 parts |
| Neocol YSK (manufactured by Dai-ichi Kogyo Seiyaku Co., Ltd.) | 1.0 part |
| Sorpol 7425 (Manufactured by Toho Chemical Industry Co., Ltd.) | 3.0 parts |
| Propylene glycol | 3.0 parts |
| Silicone KM-73 (manufactured by Shin-Etsu Chemical Co., Ltd.) | 0.5 part |
| Proxel GXL (manufactured by Zeneca Japan) | 0.1 part |
| Rhodopol 23 (manufactured by Rhone-Poulenc) | 0.02 part |
| Water | Balance |
| Total | 100 parts |

Each of the mixtures having the above-mentioned compounding ratio was finely pulverized by means of Dyno-Mill (manufactured by Bachofen AG) filled with 0.3 mm ceramic beads (Toreceram, manufactured by Toray Industries, Inc.) to prepare a suspension composition containing 40% of Compound No. 19 as fine particles having a mean particle diameter of 0.3 μm.

The compositions of Examples 1-10 were prepared by using the suspension composition thus obtained as a base.

EXAMPLE 1

| | |
|---|---|
| Base of Compound No. 19 (40.0%) | 0.44 part |
| Compound A (62.0% aqueous solution) | 50.80 parts |
| Noigen ET-129 | 10.00 parts |
| Lutensol T08 | 7.00 parts |
| Propylene glycol | 5.00 parts |
| Soprophor DSS/7-60 (manufactured by Rhodia Nikka Co.) | 1.83 part |
| N-Methyl-2-pyrrolidone | 0.15 part |
| Silicone KM-73 | 0.50 part |
| Proxel GXL | 0.10 part |
| Attagel 50 | 0.50 parts |
| Rhodopol 23 | 0.10 part |
| Water | Balance |
| Total | 100.00 parts |

A mixture of the above-mentioned formulation was thoroughly homogenized by means of a mixer such as Autohomomixer (manufactured by Tokushu Kika K.K.) or the like to obtain a suspension composition containing 0.16% of Compound No. 19 and 30% of Compound A.

EXAMPLES 2-10

Suspension concentrates were prepared by repeating Example 1, except that the alkenyl alcohol alkoxylate and the alkyl alcohol alkoxylate used in Example 1 were replaced with those shown in Table 2.

TABLE 2

| Example | Alkenyl alcohol alkoxylate Alkyl alcohol alkoxylate | Compounding Ratio (parts by weight) |
|---|---|---|
| 2 | Noigen ET-129 | 10.0 |
|   | Noigen ET-165 | 7.0 |
| 3 | Noigen ET-129 | 10.0 |
|   | Noigen ET-115 | 7.0 |
| 4 | Noigen ET-129 | 10.0 |
|   | Adekatol SO-135 | 7.0 |
| 5 | Noigen ET-129 | 10.0 |
|   | TO-347 | 7.0 |
| 6 | Pegnol O-107 | 10.0 |
|   | NK-D1107S | 7.0 |
| 7 | Noigen ET-89 | 10.0 |
|   | NK-D1107S | 7.0 |
| 8 | Noigen ET-109 | 10.0 |
|   | NK-D1107S | 7.0 |
| 9 | Noigen ET-149 | 10.0 |
|   | NK-D1107S | 7.0 |
| 10 | Noigen ET-159 | 10.0 |
|   | NK-D1107S | 7.0 |

COMPARATIVE EXAMPLE 1

A commercial preparation containing Compound A as an active ingredient (glyphosate isopropylamine salt solution) was used.

COMPARATIVE EXAMPLE 2

A composition was prepared by repeating Example 1, except that the alkyl alcohol alkoxylate was not used.

COMPARATIVE EXAMPLE 3

A composition was prepared by repeating Example 1, except that the alkenyl alcohol alkoxylate was not used.

TEST EXAMPLE 1

Barnyard grass (*Echinochloa crus-galli*) and cocklebur (*Xanthium strumarium*) were cultured in a plastic pot having a diameter of 12 cm. When the plants had reached 7-leaved stage or a later stage, a test agent solution adjusted to a prescribed concentration was sprayed, and the herbicidal effect was visually evaluated by naked eyes on the third day and twenty first day after the treatment (0: no herbicidal effect; 100: withering).

The results are summarized in Table 3.

TABLE 3

| | Compound (g/ha) | | 3 days after | | 21 days after | |
|---|---|---|---|---|---|---|
| | 19 | Compound A | Barnyard grass | Cocklebur | Barnyard grass | Cocklebur |
| Example 1 | 5.3 | 1000 | 70 | 95 | 100 | 100 |
| Example 2 | 5.3 | 1000 | 75 | 90 | 100 | 100 |
| Example 3 | 5.3 | 1000 | 75 | 95 | 100 | 100 |
| Example 4 | 5.3 | 1000 | 75 | 95 | 100 | 100 |
| Example 6 | 5.3 | 1000 | 75 | 90 | 100 | 100 |
| Example 9 | 5.3 | 1000 | 78 | 90 | 100 | 100 |
| Example 10 | 5.3 | 1000 | 78 | 90 | 100 | 100 |
| Comparative Example 1 | 0.0 | 1000 | 25 | 40 | 100 | 100 |
| Comparative Example 2 | 5.3 | 1000 | 60 | 75 | 100 | 100 |
| Comparative Example 3 | 5.3 | 1000 | 40 | 60 | 100 | 100 |

INDUSTRIAL APPLICABILITY

It has been found that, in a composition comprising a mixture of a light-induced herbicidal compound, especially a 3-substituted phenylpyrazole derivative, and an organophosphorus herbicidal compound, an excellent rapid herbicidal action and an improvement of the herbicidal effect can be achieved by incorporating an alkenyl alcohol alkoxylate and an alkyl alcohol alkoxylate into the composition.

The invention claimed is:

1. A herbicidal composition having a rapid action, containing
0.01-10 parts by weight of a light-induced herbicidal compound represented by the general formula (I-1)

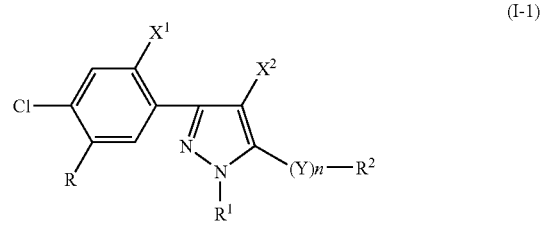

(I-1)

wherein R represents —OCH$_2$COOCH$_2$CH$_3$, R$^1$ represents —CH$_3$, R$^2$ represents —CHF$_2$, X$^1$ represents F, X$^2$ represents Cl, Y represents O, and n is 1, as a first active ingredient, 5-40 parts by weight of one or more compounds selected from N-(phosphonomethyl) glycine or a salt thereof, 4-[hydroxy(methyl)phosphino]-DL-homoalanine or a salt thereof, and 4-[hydroxy(methyl)phosphino]-L-homoalanyl-L-alanyl-L-alanine or a salt thereof, as a second active ingredient, 5-15 parts by weight of an adduct of oleyl alcohol with polyoxyethylene, as a first surfactant, and 5-15 parts by weight of one or more alkyl alcohol alkoxylates represented by the general formula (III):

$C_eH_{2e+1}$-(Eo)$_f$(Po)$_g$—OH    (III)

wherein Eo represents —O—CH$_2$CH$_2$—, Po represents —O—CH(CH$_3$)CH$_2$—, and e, f and g represent integers of 1 to 20 which are the same or different from each other, as a second surfactant, wherein a weight of the first surfactant to a weight of the second surfactant ranges from 5/1 to 1/5, and the herbicidal composition is a suspension concentrate, or an aqueous preparation.

2. The herbicidal composition according to claim 1, wherein the alkyl alcohol alkoxylate is one or more compounds selected from primary alkyl alcohol ethoxylates, primary alkyl alcohol propoxylates, primary alkyl alcohol ethoxylate propoxylates, secondary alkyl alcohol ethoxylates, secondary alkyl alcohol propoxylates, secondary alkyl alcohol ethoxylate propoxylates, tertiary alkyl alcohol ethoxylates, tertiary alkyl alcohol propoxylates and tertiary alkyl alcohol ethoxylate propoxylates.

3. A method of using a herbicidal composition characterized by treating an objective weed or a soil with an effective amount of the herbicidal composition according to claim 1, for controlling the weeds harmful to crop plants.

4. The herbicidal composition according to claim 1, further comprising polyoxyethylene distyrylphenyl ether sulfate.

* * * * *